US006355705B1

(12) United States Patent
Bond et al.

(10) Patent No.: US 6,355,705 B1
(45) Date of Patent: *Mar. 12, 2002

(54) ANAESTHETIC BONE CEMENT

(75) Inventors: David M. Bond; John F. Rudan, both of Kingston (CA)

(73) Assignee: Queen's University at Kingston, Kingston (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/825,943

(22) Filed: Apr. 1, 1997

Related U.S. Application Data

(62) Division of application No. 08/799,007, filed on Feb. 7, 1997, now abandoned.

(51) Int. Cl.$^7$ .............................................. A61L 24/06
(52) U.S. Cl. ...................... 523/118; 523/105; 523/113; 523/122; 424/422; 424/423; 424/487; 514/816; 514/817; 514/818; 623/16
(58) Field of Search ................................. 424/422, 423, 424/487; 514/816, 817, 818; 623/16; 523/105, 113, 115, 116, 117, 118, 122

(56) References Cited

U.S. PATENT DOCUMENTS

| 4,341,691 A | * 7/1982 | Anuta .......................... 523/116 |
| 4,978,391 A | * 12/1990 | Jones .......................... 523/122 |
| 5,100,241 A | * 3/1992 | Chan ........................... 366/139 |
| 5,258,420 A | * 11/1993 | Posey-Dowty et al. ...... 523/116 |
| 5,443,182 A | * 8/1995 | Tanaka et al. ............... 222/137 |
| 5,681,873 A | * 10/1997 | Norton et al. ............... 523/115 |
| 5,919,473 A | * 7/1999 | Elkhoury .................... 424/423 |
| 6,166,173 A | * 12/2000 | Mao et al. ................... 523/113 |

FOREIGN PATENT DOCUMENTS

| AU | 55167/86 | 5/1986 |
| EP | 0164483 | 12/1985 |
| JP | 53-015409 | 2/1978 |
| JP | 1-143829 | 6/1989 |

OTHER PUBLICATIONS

Puronto, Marjukka. *Anaesthesist*, vol. 24: 408–411, 1975.*
Tryba et al., *Anaesthesist*, vol. 40: 25–32, 1991.*
Zawadzki et al., *Anaesth. Resus. Inten. Therap.*, vol. 4, No. 3: 181–185, 1976.*

The Sustained Release of Antimicrobial Drugs from Bone Cement, An Appraisal Of Laboratory Investigations And Their Significance, R. Bayston, R.D.G. Milner, 1982.
Antibiotic Impregnated Bone Cement in Total Hip Arthroplasty, An In Vivo Comparison of the Elution Properties of Tobramycin and Vancomycin, William W. Brien, M.D., Eduardo A. Salvati, M.D., Renata Klein, Ph.D., Barry Brause, M.D., and Steven Stern, M.D., 1993.
Cephalosporins in Bone Cement, Studies In Vitro and In Vivo, Sean Hughes, Christine A. Field, Margaret R.K. Kennedy, C.H. Dash, Feb. 1979.
The Role of Antibiotic–Loaded Cement in the Treatment of an Infection After a Hip Replacement, Clive P. Duncan, M.D., F.R.C.S, Bassam A. Masri, M.D., 1994.
Standard Specification for Acrylic Bone Cement, Designation F451–95, ASTM Subcommittee F04.11, 1995.
Badner, N.H. et al., "Intra–articular injection of bupivacaine in knee–replacement operations", *J. Bone and Joint Surgery Inc.* 78–A:734–738 (1996).
Baker, A.S. et al., "Release of gentamicin from acrylic bone cement", *J. Bone and Joint Surgery, Inc.* 70–A:1551–1557 (1988).
Hadgraft, J. et al., "Calculations of drug release rates from controlled release devices. The slab", *Interntl. J. Pharma.* 2:177–194 (1979).
Law, H.T. et al., "In vitro measurement and computer modelling of the diffusion of antibiotic in bone cement", *J. Biomed. Eng.* 8:149–155 (1986).
Ravin, C.E., et al., "in vitro effects of lidocaine on anaerobic respiratory pathogens and strains of *Hemophilus influenzae*" *Chest* 72:439–441 (1977).
Rosenburg, P.H., et al., "Antimicrobial activity of bupivacaine and morphine", *Anesthesiology* 62: 178–179 (1985).
Schmidt, R.M. et al., "Antimicrobial activity of local anesthetics: lidocaine and procaine", *J. Infect. Dis.* 121: 597–607 (1970).
Wasserlauf, S. et al., "The release of cytotoxic drugs from acrylic bone cement", *Hospital for Joint Diseases* 53:68–74 (1993).

* cited by examiner

*Primary Examiner*—Peter Szekely
(74) *Attorney, Agent, or Firm*—Stephen J. Scribner; Carol Miernicki Steeg; Elizabeth A. Hanley

(57) ABSTRACT

A polymethacrylate or other bone cement composition having analgesic properties is described. Bone cements containing up to 5% by weight of a local anaesthetic agent, such as lidocaine, have been demonstrated to elute sufficient lidocaine to provide an analgesic effect in vivo.

6 Claims, 3 Drawing Sheets

ANAESTHETIC BONE CEMENT

The present application is a divisional of, and claims priority to, U.S. Patent application Ser. No. 08/799,007 filed on Feb. 7, 1997, the contents of which are expressly incorporated herein by reference.

FIELD OF THE INVENTION

This invention relates to surgical bone cement compositions and more particularly to bone cement compositions having anaesthetic properties, and to methods for producing local analgesia.

BACKGROUND OF INVENTION

Polymer based surgical bone cements have been used for many years to fill voids in bones and to improve fixation of implanted orthopaedic prosthetic devices. Typically such cements contain polymers or copolymers of alkyl methacrylate and/or copolymers of methyl methacrylate with methyl acrylate or styrene. The liquid compound consisting of esters of acrylic or methacrylic acid (typically methyl methacrylate) is packaged in an ampoule, possibly with additives such as premature polymerization preventers such as hydroquinone, and curing promoters such as N,N-dimethyl-p-toluidine. A polymerization initiator, typically an organic peroxy compound such as powdered benzoyl peroxide, is combined with the polymeric component and radiopacifier (such as barium sulphate or zirconium dioxide). The polymeric materials are generally sterilized by either irradiation or gas sterilization. In use, typically a bone is cut and prepared to receive a surgical implant and then the liquid and dry components of the cement, contained in the ampoule and a powder bag are mixed together to form a paste which can then be applied by the surgeon to the cut bone. The implant can then be set in the paste which, when fully polymerized, forms a continuous solid interface between the implant and the bone.

It is also known to incorporate therapeutic or diagnostic substances into the bone cement for various purposes. For example, U.S. Pat. No. 4,900,546, issued Feb. 13, 1990 to Poseyn Dowty et al, teaches the incorporation of antibiotics such as gentamycin, penicillin and tetracycline; anti-cancer drugs; anti-inflammatory drugs; immuno-stimulants; immuno-suppressants; osteogenic promoters and diagnostic substances such as radioactive tracers. While anti-inflammatory drugs may be defined as analgesics, such compounds are not anaesthetic agents.

Although local anaesthetics, such as lidocaine and prilocaine are known to have potent anti-microbial activity (anti-bacterial and anti-fungal), when used in relatively high dosages (0.5–2% solution) (*J. Infect. Diseases*, Vol 121, No. 6,597–607, June 1970), heretofore such anaesthetic compounds have not been incorporated into bone cements for the promotion of anaesthesia. It has now been found that substantial pain relief can be achieved by incorporating into a known bone cement composition a local anaesthetic agent at a dosage level several orders of magnitude lower than would be required to achieve an anti-microbial effect with such agent.

OBJECT OF INVENTION

An object of the present invention is to provide novel bone cement compositions, having anaesthetic properties, which incorporate an analgesic. Another object of this invention is to provide a method for producing analgesia adjacent to a bone end.

BRIEF STATEMENT OF INVENTION

By a broad aspect of this invention, there is provided an anaesthetic bone cement comprising a bone cement composition including an effective amount up to about 5% by weight of a local anaesthetic agent.

By a preferred aspect of this invention, there is provided an anaesthetic bone cement composition comprising: (a) a liquid monomeric (meth)acrylate composition; (b) a powder comprising at least one of a homopolymer and a copolymer of methyl methacrylate containing an effective amount of a polymerization initiator and a radiopacifier; and (c) an effective amount up to about 5% by weight of said bone cement composition of a local anaesthetic agent.

By another aspect of this invention, there is provided a process for the production of an anaesthetic bone cement comprising combining: (a) a liquid monomeric (meth)acrylate; (b) a powdered component comprising at least one of a homopolymer and a copolymer of methyl methacrylate, an effective amount of a polymerization initiator and a radiopacifier; and (c) an effective amount up to about 5% by weight of a local anaesthetic agent.

By yet another aspect of this invention there is provided a method for producing analgesia at an orthopaedic implant site in a patient, comprising cutting and preparing bones at said site to receive said implant and applying to said prepared bones a bone cement composition comprising: (a) a liquid monomeric (meth)acrylate composition; (b) a powder comprising at least one of a homopolymer and a copolymer of methyl methacrylate containing an effective amount of a polymerization initiator and a radiopacifier; and (c) an effective amount up to about 5% by weight of said bone cement composition of a local anaesthetic agent.

DETAILED DESCRIPTION OF PREFERRED EMBODIMENTS

Local anaesthetic agents are generally amides or ester compounds which act to block neural receptors and thus deaden or block pain. NSAID analgesic compounds such as aspirin or acetaminophen act in an entirely different manner to provide analgesia but not anaesthesia. As used herein, the term "analgesia" means an absence of normal sensibility to pain without affecting consciousness, and the term "anaesthesia" means total or partial loss of sensation induced by administration of a drug. The present invention is concerned with the use of local anaesthetic agents, such as lidocaine, bupivacaine, prilocaine (amide family), and tetracaine (ester family) to provide an analgesic effect in body tissues surrounding a surgical site in which a bone cement has been employed. A preferred anaesthetic agent is Xylocaine® (Astra Pharmaceuticals) brand of lidocaine.

In order to determine whether local anaesthetics, such as lidocaine, elute from a bone cement containing from about 2.0% to about 5.0% by weight anaesthetic, a series of elution studies were performed.

Figure 1:
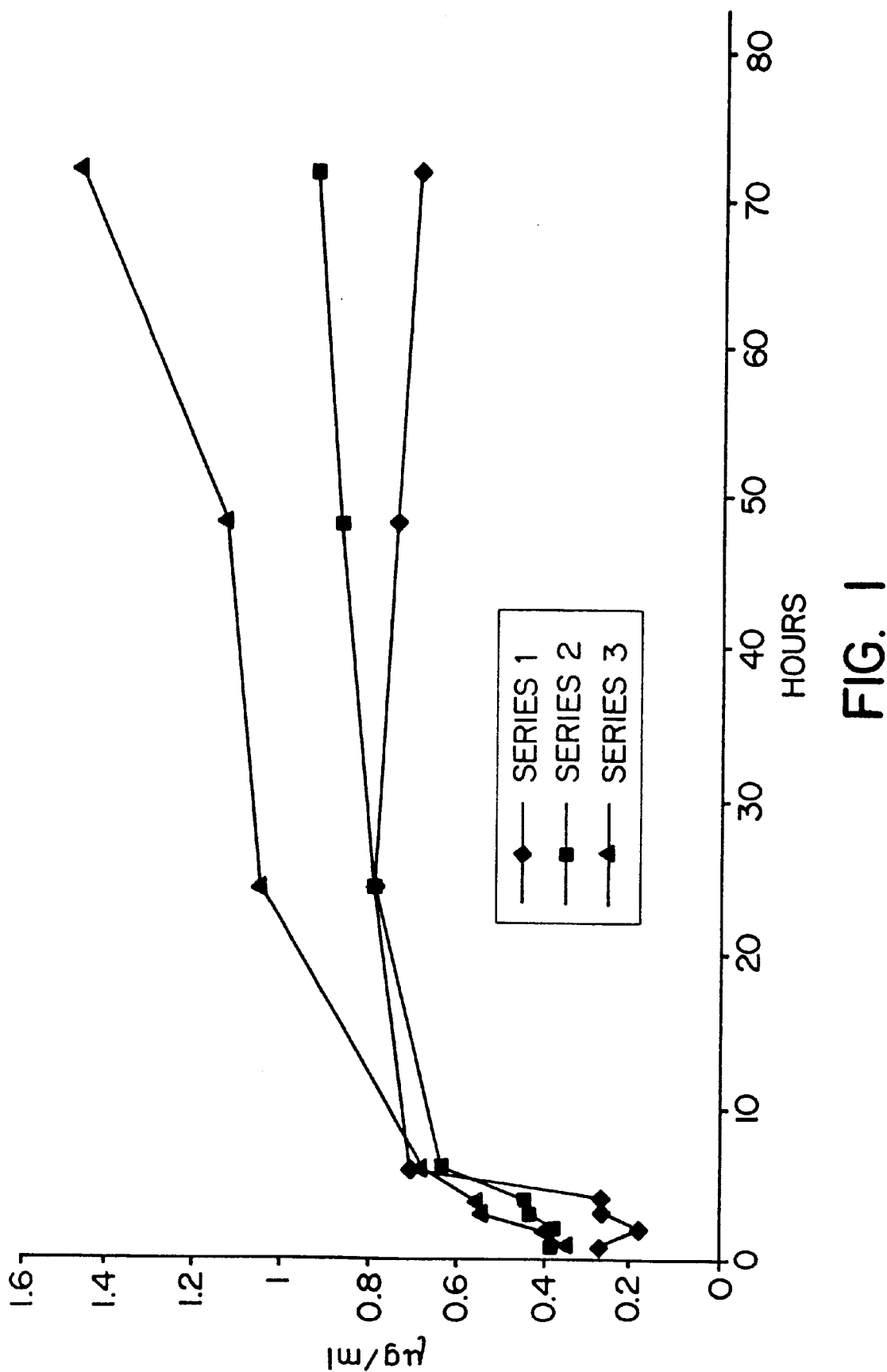
FIG. 1 is a graph showing accumulation of lidocaine from Howmedica Cement.
Figure 2:
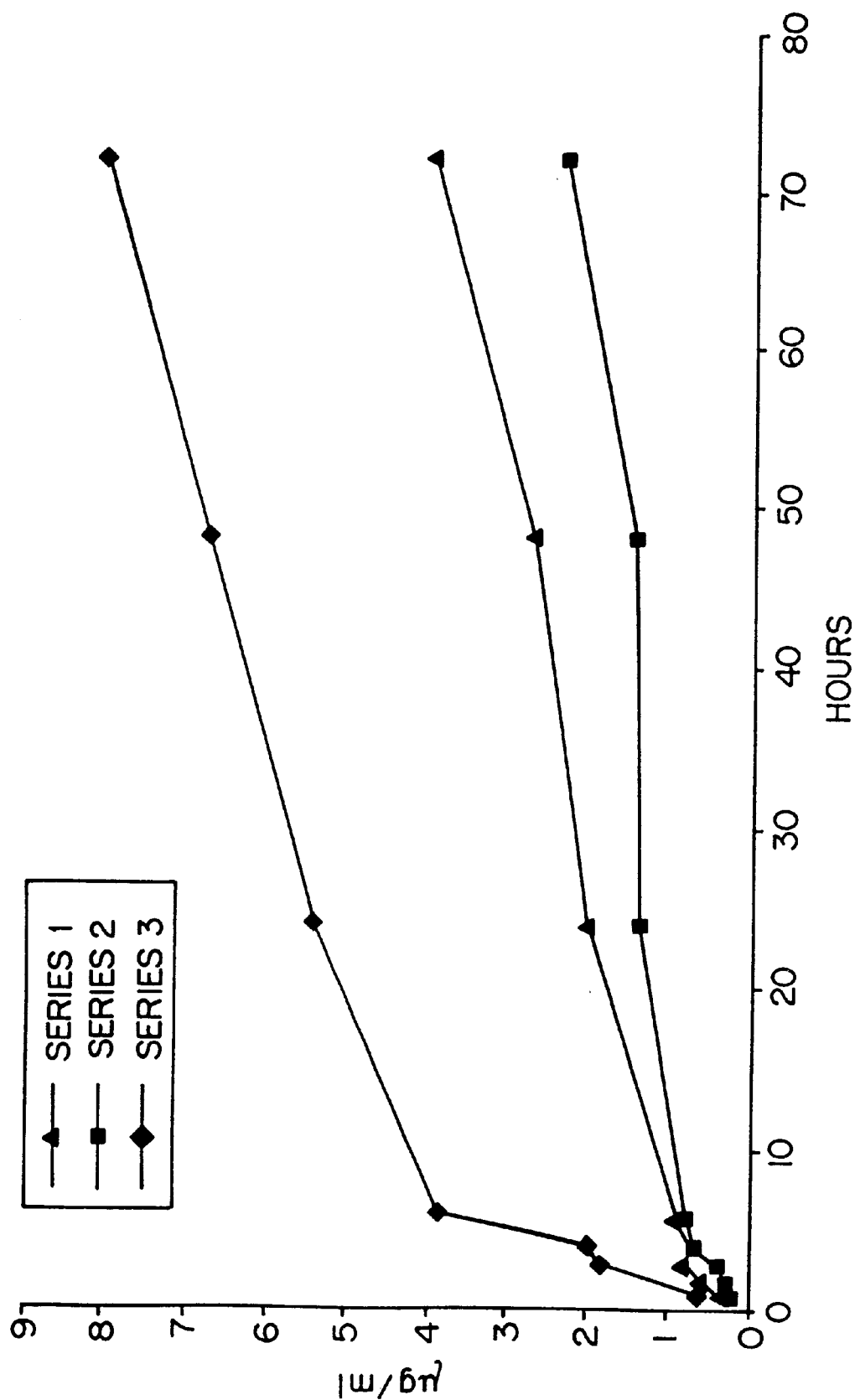
FIG. 2 is a graph showing accumulation of lidocaine from Zimmer Cement.
Figure 3:
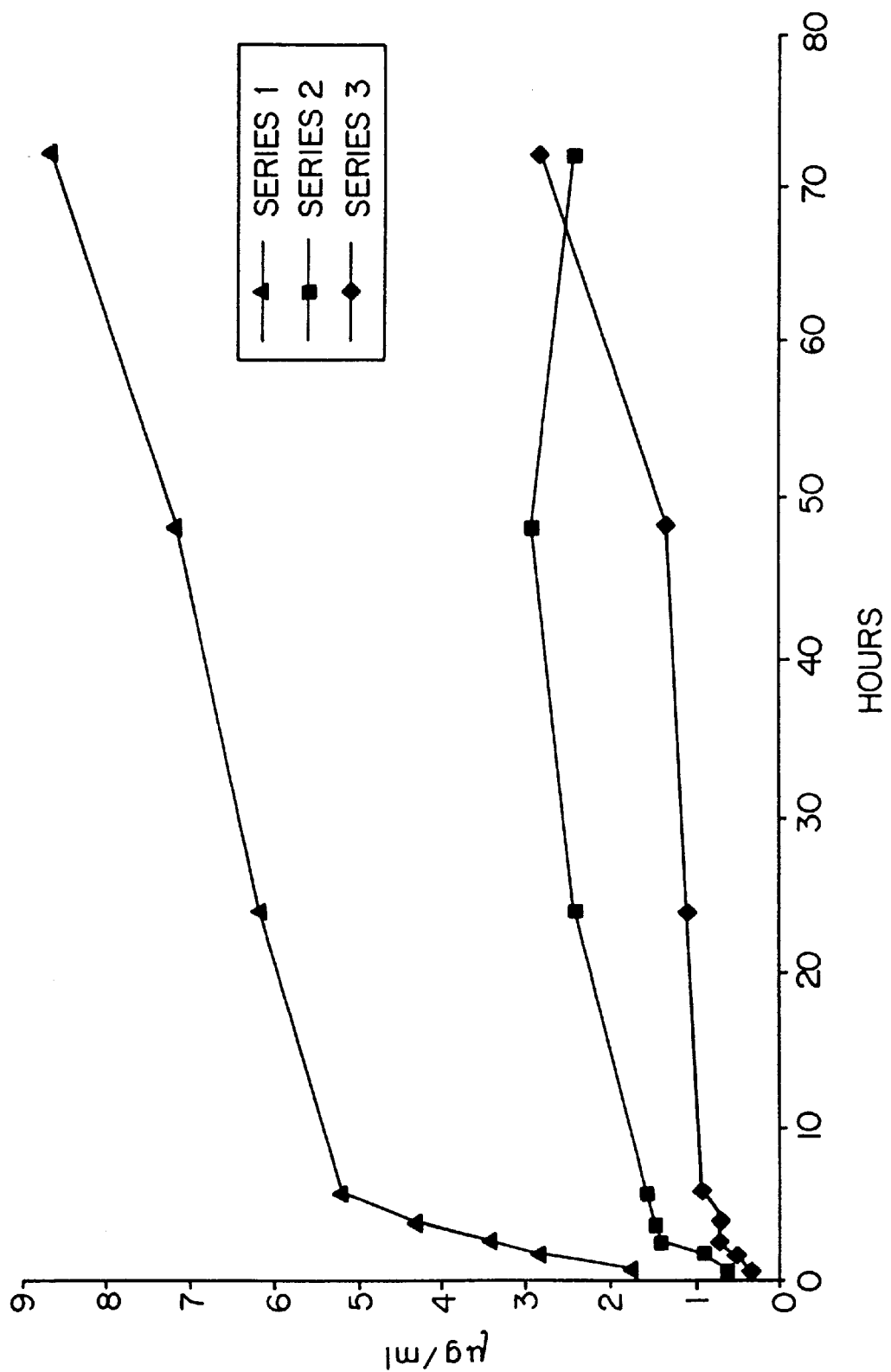
FIG. 3 is a graph showing accumulation of lidocaine from DePuy CMW Cement.

Method 40 g ampoules of bone cement from each of three manufacturers: Howmedica (Simplex® bone cement), Zimmer (Osteobond) and DePuy (CMW3 bone cement), were mixed with 0.5, 1.0 and 2.0 g of gas sterilized lidocaine (Xylocaine®, Astra Pharmaceutical). The polymerization initiated mixtures were formed into discs 50 mm×1 mm and allowed to harden. The hardened discs were then placed in a stirred solution (100 ml) containing 0.2% saline at 37° C. 100 μl aliquots were taken at 1, 2, 3, 4, 6, 24, 48 and 72 hours and HPLC with electrochemical detection analysis was performed to determine the lidocaine level in each sample. Results Typical elution profiles are shown in FIGS. 1 (Howmedica), 2 (Zimmer) and 3 (DePuy). From these profiles it may be concluded that lidocaine elutes from the bone cement mixture in an amount proportional to the amount of lidocaine in the mixture. The rate of elution is at a maximum during the first 24 hours and then tapers off. The curves also indicate that there is a peak dose at about the 6 hour point. The peak dose then provides sustained release over a 72-hour test period. It may also be concluded that elution occurs mainly from the surface of the disc and related to the porosity and other surface properties of the disc.

EXAMPLE 1

A female patient, 68 years old, having a previous total knee replacement and a below-the-knee amputation, presented with latent infection in the knee. A revision to remove the knee prosthesis was performed and the cut ends of the bone were treated with an anti-bacterial bone cement to keep the bones spaced. Three weeks later, the bone cement was removed and tissue samples were taken for laboratory analysis for signs of infection. Bone cement was temporarily applied to keep the bones spaced and aligned, but this time the cement was Howmedica bone cement containing 2 g of lidocaine (Xylocaine®) per 40 g package of cement. The lidocaine laden-cement was gas sterilized but not irradiated. After recovery from anaesthesia the patient reported severe pain in the knee for a period of approximately 6 hours and thereafter no pain at all. 24 hours post surgery, the patient was sleeping without the aid of pain killers and was also able to receive physiotherapy without feeling undue discomfort.

From this example, it appears that lidocaine is eluted from bone cement and within 6 hours of placement, sufficient lidocaine has eluted to provide an analgesic effect which persists for at least 24 hours and probably at least several days before it metabolizes in the body.

The effects of lidocaine on the mechanical properties of CMW3 bone cement have also been evaluated and are summarized in table 1 below.

TABLE 1

| Cement Property | CMW3 | CMW3 + Lidocaine |
|---|---|---|
| Dough time (min:sec) | 2:50 | 7:05 |
| Setting time (min:sec) | 10.06 | 14.20 |
| Exotherm (° C.) | 70.8 | 69.1 |
| Compressive strength (Mpa) | 112.0 | 113.3 |
| Flexural strength (Mpa) | 65.0 | 66.3 |
| Flexural modulus (Mpa) | 2785 | 2753 |
| Impact strength (J/m) | 3.03 | 3.61 |

From the table it can be seen that addition of lidocaine to CMW3 improves impact strength by about 10%, but has little effect on compressive strength, flexural strength or flexural modulus. It is particularly noted that lidocaine additions increase the cement setting time by about 40% and the "doughing time," i.e., the time needed to reach a working mix that can be readily handled by a factor of 3.

It will, of course, be appreciated that other proprietary bone cements can equally well be employed including CMW® Endurance™ by DePuy or Palacos®R which is distributed by Schering Plough in Europe and by Richards in North America. The local anaesthetics of the present invention may also be incorporated into proprietary bone wax compositions, such as Ethricon® Bone Wax, which is a sterile mixture of beeswax and isopropyl palmitate, a wax softening agent used to control bleeding from bone surfaces. The local anaesthetics may also be incorporated into injectable bone substitutes, or bone paste, such as Norican Skeletal Repair System (Norican SRS) developed by Norican Corp. of Cupertino, Calif. which is a calcium phosphate based cement which, when injected, forms carbonated apatite.

We claim:

1. A method for producing analgesia at an orthopaedic implant site in a patient, comprising the step of:

applying an anaesthetic bone cement composition to a bone and an orthopaedic implant at an orthopaedic implant site in a patient so that analgesia is provided at said orthopaedic implant site and release of a local anaesthetic agent from said bone cement composition in the patient does not substantially change the strength of the bone cement, wherein said anaesthetic bone cement composition was prepared by combining (a) a powder comprising at least one of a homopolymer and a copolymer of methyl methacrylate, (b) an effective amount of a polymerization initiator, (c) an amount up to about 5% by weight of said local anaesthetic agent and (d) a liquid monomeric (meth)acrylate composition.

2. A method according to claim 1, wherein the anaesthetic agent is combined with the powder before the liquid monomeric (meth)acrylate composition is combined with the powder.

3. A method according to claim 1, wherein said preparing step further comprises combining a radiopacifier with the powder, the polymerization initiator, the local anaesthetic agent, and the liquid monomeric (meth)acrylate composition.

4. A method according to claim 1, wherein said preparing step further comprises irradiating or gas sterilizing the bone cement composition.

5. A method according to claim 1, wherein said anaesthetic agent is selected from the group consisting of lidocaine, bupivacaine, prilocaine and tetracaine.

6. A method according to claim 1, wherein said bone cement composition contains up to 2.5% by weight of the local anaesthetic agent.

* * * * *